United States Patent [19]

Molnar et al.

[11] 4,117,160
[45] Sep. 26, 1978

[54] PHENOXY COMPOUNDS AND COMPOSITIONS

[75] Inventors: Francois Molnar, Valais; Suzanne Szabo, Vaud; Peter Radanow Statkov, Geneva, all of Switzerland

[73] Assignee: Cermol S.A., Switzerland

[21] Appl. No.: 813,985

[22] Filed: Jul. 8, 1977

[30] Foreign Application Priority Data

Jul. 19, 1976 [CH] Switzerland ............... 9217/76

[51] Int. Cl.$^2$ ............... A01N 9/20; C07C 93/06
[52] U.S. Cl. ............... 424/316; 260/501.17; 260/570.7; 424/330
[58] Field of Search ............... 260/501.17, 570.7 R, 260/570.7; 424/316, 330

[56] References Cited

U.S. PATENT DOCUMENTS

| 2,738,351 | 3/1956 | Dickison et al. | 260/570.7 X |
| 2,895,995 | 7/1959 | Willey et al. | 260/570.7 X |
| 3,740,397 | 6/1973 | Lafon | 260/570.7 X |
| 3,839,464 | 10/1974 | Najer et al. | 260/570.7 X |

Primary Examiner—Robert V. Hines
Attorney, Agent, or Firm—Stevens, Davis, Miller & Mosher

[57] ABSTRACT

New glycerol 1,2-bis-aminoalkyl ethers corresponding to the formula

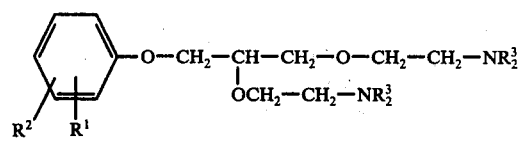

and their salts, in which $R^1$ represents a $C_{1-3}$alkyl, $C_{1-3}$alkoxy, trifluoromethyl group or a halogen, $R^2$ represents hydrogen, a halogen, a $C_{1-3}$alkyl, $C_{1-3}$alkoxy group, and $R^3$ represents a $C_{1-3}$alkyl group, having local anesthetic and anti-arrhythmic properties.

6 Claims, No Drawings

PHENOXY COMPOUNDS AND COMPOSITIONS

The therapeutic effects of basic 1-aryloxy-3-alkoxy-propan-2-ols has been known for a long time (see British Pat. No. 560,568 of 1940). These compounds have remarkable sedative, hypnotic and analgesic effects. Recently, it has been found that one such compound, namely 1-(β-diethylaminoethoxy-3-o-methoxyphenoxypropan-2-ol) has a favorable reaction on disturbances of the cardiac rhythm (see German Offenlegungsschrift No. 24.31.126).

New compounds according to the invention are 3-phenoxy-1,2-bis-aminoalkoxypropanes having the general formula

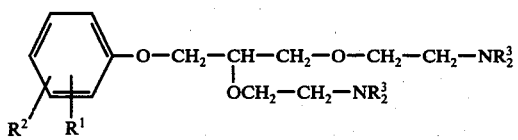

in which $R^1$ represents $C_{1-3}$alkyl, $C_{2-3}$alkenyl, $C_{1-3}$alkoxy, trifluoromethyl or halogen, $R^2$ represents hydrogen, halogen, $C_{1-3}$alkyl, $C_{2-3}$alkenyl, or $C_{1-3}$alkoxy, and $R^3$ represents a $C_{1-3}$alkyl group, together with their salts with acids.

These compounds have useful local anaesthetic and anti-arrhythmic properties and therapeutic compositions according to the invention comprise such a compound and pharmaceutically acceptable carrier.

The salts may be formed with mineral acids such as hydrochloric acid or organic acids such as fumaric, maleic, tartaric, citric, orotic or oxalic acid. These salts are generally very soluble in water and permit different forms of application for pharmacological and medical treatments.

Preferred values for $R_1$ and $R_2$ include methyl, ethyl, propyl, methoxy, allyl, chloro and bromo, but it is often preferred that $R_2$ is hydrogen and also $R_1$ may be trifluoromethyl. Preferably all four radicals $R_3$ are the same, often methyl.

The new compounds are 3-phenoxy-1,2-bis-aminoalkyl ethers of glycerol and may be prepared by a conventional etherification process from known compounds. A preferred method comprises reaction of one mol of a compound:

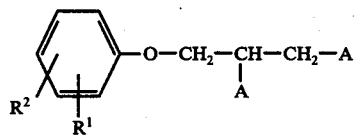

with two mols of a compound

in which $R^1$, $R^2$ and $R^3$ have the same significances as above and A and B represent in the one case a halogen, preferably chlorine or bromine atom and in the other case the group -OAlk, in which Alk significes an alkali metal. Thus it is possible to react either sodium 3-phenoxy-1,2-propane diolate with the dialkylamino-ethyl halide, or 3-phenoxy-1,2-dihalopropane with sodium dialkylamino-ethanolamate.

A preferred way of performing the process comprises reacting a sodium alcoholate of formula II and a halide of formula III in an anhydrous solvent, filtering the salts formed, driving the solvent off under vacuum, purifying the crude product by solubilising it in dilute hydrochloric acid and extracting the insoluble portion, alkalising the aqueous layer and then extracting the base and finally distilling under vacuum. Preferably in this process an excess of 10 to 50% of the compound of formula III is used (i.e. 2.2 to 3 moles of the compound of formula III are used per mole of compound of formula II).

The process is best conducted with the compounds to be reacted in suspension in a suitable amount of an organic solvent, for example dry toluene, anhydrous dimethylformamide, or diisopropyl ether.

The reaction may be carried out by introducing a solution of the halogen derivative into the suspension of the sodium alcoholate salt previously prepared at a temperature between 40° and 60° C. and then heating between 80° and 110° C. to complete the reaction. Thus the reaction is preferably conducted in the temperature range 40° and 130° C. The duration of the reaction preferably is between 8 and 25 hours.

When the desired compound is to be in the form of a salt this may be made by treating 1 mol of the compound of formula I in an organic solvent with two mols of an acid dissolved in an alcohol and then precipitating the salt if necessary by adding an apolar solvent.

The compounds of the present invention have, in therapeutic doses, local anaesthetic as well as anti-arrhythmic properties. They correct and oppose symptoms of disturbances in the cardiac rhythm. Compared to various reference products, the new compounds produce a more lasting local anaesthesia, they oppose experimental cardiac trouble in a more effective manner (that is to say the therapeutic effect obtained with smaller doses is more lasting) and there is a greater difference between therapeutically useful doses and doses which cause undesirable secondary effects.

The invention is illustrated in greater detail by the following non limiting Examples.

EXAMPLE 1

39.2 g (0.2 mol) of 2,6-dimethylphenoxy-glycerine ether are placed in a 1-liter reaction vessel equipped with a stirrer, a thermometer and a condenser with a $CaCl_2$ tube and solubilized in 140 ml of dry toluene. To this solution, at 50° C., there are added, in small portions, 18.4 g (0.4 mol) of a 55% dispersion of NaH in oil and the mixture is then kept under reflux for 4 hours. After cooling to 40° C., 0.6 mol of a 20% solution of dimethylaminoethyl chloride dissolved in dry toluene is introduced in 1 hour with the aid of a dropping funnel and the mixture is then stirred under reflux for 18 hours. Finally, the mixture is left to cool, the mineral salts are filtered off and the mother liquors are evaporated. The residue (76.7 g) is washed, by solubilizing it in aqueous HCl, with ethyl acetate, the aqueous layer is treated with activated carbon, this is filtered off, alkalization is carried out with a concentrated ammonia solution and the base is extracted with chloroform. Drying and then evaporation of the chloroform phase under vacuum are then carried out and the base (55.5 g) is then distilled under a vacuum of 1 mm Hg. 32 g of main fraction, b.p. 187°-196° C., are obtained, which corresponds to a yield of 52.5%. By dissolving this base in ethyl acetate and gaseous HCl in solution, the dihydrochloride of 1,2-bis-dimethylaminoethoxy-3-(2',6'-dimethylphenoxy)-propane crystallizes. Melting point of these hygroscopic crystals: 150°–152° C.

EXAMPLE 2

A solution of 39.8 g (0.2 mol) of guaiacol-glycerine ether dissolved in 80 ml of anhydrous dimethylformamide is introduced, by means of a dropping funnel, into a suspension of 9.6 g of sodium hydride (0.4 mol) in 120 ml of anhydrous dimethylformamide. The introduction lasts for 4 hours and the temperature varies between 40° and 60° C. The mixture is agitated without heating until the evolution of hydrogen ceases and then a solution of 0.6 mol of dimethylaminoethyl chloride dissolved in diisopropyl ether is introduced with the aid of a dropping funnel in such manner that the temperature does not exceed 60° C. The diisopropyl ether is then distilled off and the mixture is heated at 90° C. for 15 hours. Following the same method of separation and purification described in Example 1, 35.1 g of 1,2-bis-dimethylaminoethoxy-3-(2'-methoxyphenoxy)-propane are distilled at 182°–190° C. under a vacuum of 0.4–0.6 mm Hg. By dissolving this base in 300 ml of ethyl acetate and treating it with a solution of 26.0 g of oxalic acid in 100 ml of absolute ethanol, 48.5 g of dioxalate are obtained. M.p.: 95°–98° C.

EXAMPLE 3

A solution of 32.4 g (0.1 mol) of 1-2'-methoxyphenoxy-2,3-dibromopropane in 50 ml of dry toluene is introduced by means of a dropping funnel into a suspension of 0.25 mol of sodium diethylaminoethanolate in 100 ml of dry toluene and the mixture is then kept under reflux for 13 hours. By proceeding with the same treatment as is described in Example 1, 1,2-bis-diethylaminoethoxy-3-(2'-methoxyphenoxy)-propane is distilled at 168°–175° C. under a vacuum of 0.1–0.2 mm Hg.

By methods corresponding to those in Examples 1 to 3, the following products can be synthetized:
(1) 1,2-bis-dimethylaminoethoxy-3-(3'-trifluoromethylphenoxy)-propane m.p. of the diorotate-dihydrate: 102°–105° C.
(2) 1,2-bis-dimethylaminoethoxy-3-(2'-methoxy-4'-bromo-phenoxy)propane dihydrochloride m.p. at 145°–146° C.
(3) 1,2-bis-diethylaminoethoxy-3-(2',4'-dichlorophenoxy)-propane b.p.: 180°–184° C. at 0.2 mm Hg.
(4) 1,2-bis-diisopropylaminoethoxy-3- (2'-methoxy-4'-propyl-phenoxy)-propane b.p.: 224°–230° C. at 0.4 mm Hg.
(5) 1,2-bis-dimethylaminoethoxy-3-(2'-allyloxy)-phenoxypropane ditartrate: m.p.: 69°–74° C.
(6) 1,2-bis-dimethylaminoethoxy-3-(4'-methoxyethylphenoxy)-propane maleate m.p.: 98°–101° C.

The acute toxicity of the compounds to which the present invention relates has been examined in albino mice and rats. The active compound was administered in the form of an aqueous solution.

On oral administration to mice, the $LD_{50}$ of the most active compounds is around 550 mg/kg.

On intraperitoneal administration to rats, the $LD_{50}$ is about 250 mg/kg.

The most active compounds of the invention have a particularly interesting local anaesthetic activity. Thus, in experiments carried out on the sciatic nerve of rats, their activity is at least twice more lasting than that of lidocaine, and contrary to lidocaine, these compounds do not cause toxic reactions to the central nervous system at doses only slightly higher than those having a therapeutic effect.

The anti-arrhythmic activity of the compounds according to the invention has been tested on different examples of experimental arrhythmy. Thus, the arrhythmy caused by the intravenous introduction of aconitine into rats is corrected by the intravenous administration of the said compounds. The increase in the effect increases in parallel with the increase in the dose.

The most active compounds also act orally.

In comparison with other anti-arrhythmic products such as, for example, lidocaine and ajmaline, these preferred new compounds show a greater effectiveness. For example, in the aconitine arrhythmy test with rats, the $ED_{50}$ of these compounds is around 2 mg/kg, while that of lidocaine is distinctly above 5 mg/kg.

At the same time, the average fatal dose for rats on constant and continual intravenous infusion (2 mg/0.1 ml/1 mn) of these compounds is around 150 mg/kg, while under identical conditions the fatal dose in the case of lidocaine is about 34 mg/kg.

The most active new compounds also have a negative inotropic activity which is very low and distinctly lower than that of lidocaine and ajmaline.

They are also less hypotensive and distinctly better tolerated.

What is claimed is:

1. A compound of the formula

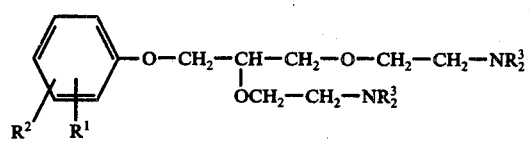

I in which $R^1$ represents $C_{1-3}$alkyl, $C_{2-3}$alkenyl, $C_{1-3}$alkoxy, trifluoromethyl or halogen, $R^2$ represents hydrogen, halogen, $C_{1-3}$alkyl, $C_{2-3}$alkenyl, $C_{1-3}$alkoxy group, and $R^3$ represents a $C_{1-3}$alkyl group, or a salt thereof.

2. A compound according to claim 1 in which $R^1$ and $R^2$ are individually selected from methyl, ethyl, propyl, methoxy, allyl, chloro or bromo or $R^1$ is trifluoromethyl or $R^2$ is hydrogen, and in which all four radicals $R^3$ are the same.

3. A compound of claim 1 of the formula:

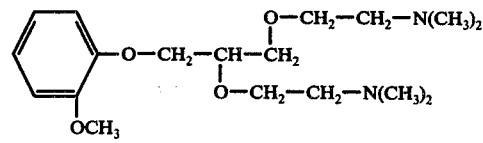

or a pharmaceutically acceptable salt thereof.

4. A compound of claim 1 of the formula:

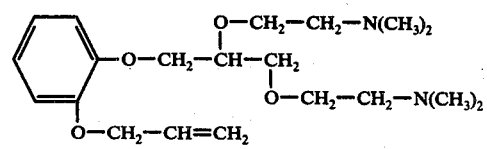

or a pharmaceutically acceptable salt thereof.

5. A pharmaceutical composition comprising a compound of claim 1 in a local anesthetically effective amount and a pharmaceutically acceptable carrier therefor.

6. A method of providing a local anesthetic effect to a subject which comprises administering to said subject a local anesthetically amount of a compound of claim 1.

* * * * *